US005939024A

United States Patent [19]

Robertson

[11] Patent Number: 5,939,024

[45] Date of Patent: Aug. 17, 1999

[54] MICROPLATE ASSEMBLY

[75] Inventor: James E. Robertson, Minooka, Ill.

[73] Assignee: Packard Instrument Co., Downers Grove, Ill.

[21] Appl. No.: 08/997,182

[22] Filed: Dec. 23, 1997

[51] Int. Cl.[6] .............................. C12M 1/12; C12M 1/20

[52] U.S. Cl. ...................................... 422/101; 435/288.5

[58] Field of Search ............................ 422/99, 101, 102, 422/104; 356/246, 440; 435/288.4, 288.5

[56] References Cited

U.S. PATENT DOCUMENTS

| | | | |
|---|---|---|---|
| 4,498,780 | 2/1985 | Banno et al. | 356/414 |
| 4,678,326 | 7/1987 | Harjunmaa | 356/73 |
| 4,948,442 | 8/1990 | Manns | 156/73.1 |
| 5,039,493 | 8/1991 | Oprandy | 422/101 |
| 5,047,215 | 9/1991 | Manns | 422/101 |
| 5,082,628 | 1/1992 | Andreotti et al. | 422/82.08 |
| 5,141,719 | 8/1992 | Fernwood et al. | 422/101 |
| 5,298,753 | 3/1994 | Sonne et al. | 250/364 |
| 5,319,436 | 6/1994 | Manns et al. | 356/246 |
| 5,326,533 | 7/1994 | Lee et al. | 422/101 |
| 5,342,581 | 8/1994 | Sanadi | 422/101 |
| 5,516,490 | 5/1996 | Sanadi | 422/101 |
| 5,529,756 | 6/1996 | Brennan | 422/131 |
| 5,609,826 | 3/1997 | Cargill et al. | 422/99 |
| 5,609,827 | 3/1997 | Russell et al. | 422/102 |
| 5,759,494 | 6/1998 | Szlosek | 422/102 |

*Primary Examiner*—Jeffrey Snay
*Attorney, Agent, or Firm*—Arnold, White & Durkee

[57] ABSTRACT

A microplate assembly for use in analyzing samples captured on a filter medium comprises a holding tray and a collimator having multiple sample wells. These elements are generally rectangular in shape and are sized to stack on top of one another. The filter medium is positioned within the holding tray and the holding tray is positioned within the collimator with the filter medium positioned beneath the collimator. To prepare samples in the microplate assembly for analysis, the samples are captured on the filter medium and the filter medium is placed in the holding tray. After adding scintillation cocktail or luminescent substrate to the filter medium, the collimator is placed over the holding tray with the filter medium positioned between the collimator and the holding tray and the samples disposed in the sample wells. The holding tray, the filter medium and the collimator are provided with complementary keyed corners to facilitate alignment of these elements relative to one another. The wells of the collimator include respective lower rims protruding into the filter medium to minimize crosstalk through the filter medium. The collimator and holding tray include structure for defining multiple positions of engagement with each other for accommodating filters of different thicknesses.

22 Claims, 3 Drawing Sheets

MICROPLATE ASSEMBLY

FIELD OF THE INVENTION

The present invention relates generally to multi-well sample trays which are commonly referred to as microplates and which are used to hold a large number (e.g., 24, 48, 96, or more) of samples in a standardized format to be assayed by various techniques such as autoradiography, liquid scintillation counting (LSC), luminometry, etc. In particular, the present invention relates to a microplate assembly and method which permits a filter medium chosen by a user to be placed in the microplate assembly for analysis and counting.

BACKGROUND OF THE INVENTION

Many microplate assays important in drug research, molecular biology, and biotechnology involve the binding or uptake of radioisotopic or luminescent tracers to target macromolecules or whole cells to form labelled complexes. Examples of microplate assays include DNA and RNA hybridizations (e.g., dot blots), enzyme activity assays (e.g., reverse transcriptase and kinases), receptor binding assays, and cell proliferation assays. A common feature of all these assays is that a labelled complex must be separated from any excess tracer that does not react with the target macromolecules or whole cells during the binding process. This is typically done by capturing or immobilizing the labelled complex on a suitable filter medium and washing away the unreacted tracer. Once separated, the material captured on the filter medium is typically assayed by autoradiography, liquid scintillation counting (LSC), or luminometry. In some cases, the filter medium is used to specifically bind the assay components, while in other cases the filter medium is used as a filtration medium. Typical filter materials include glass fiber, nylon, nitrocellulose, phosphocellulose, or other suitable material.

One technique for assaying samples captured on a filter medium requires the individual samples to be cut from the filter medium and counted in individual scintillation vials using a liquid scintillation counter (LSC). A drawback of this technique is that the analysis and quantitation of bound samples immobilized on the filter medium requires time consuming sample preparation. In addition, this technique is expensive because the individual scintillation vials containing large volumes of scintillation fluid are discarded following use.

Another technique for assaying samples captured on a filter medium encloses the filter medium in a sample bag, treats the filter medium with scintillation liquid, and places the bag containing the treated filter medium into a scintillation counter. To reduce crosstalk between the samples on the filter medium during analysis, the filter medium itself is provided with a printed crosstalk reducing pattern. An example of such a technique is the 1205 Betaplate system manufactured by Wallac Oy of Turko, Finland. While this technique substantially reduces the amount of time for sample preparation and analysis, the technique generally requires a user to employ special non-standard filters available only from the manufacturer of the scintillation counter.

The 1205 Betaplate system, for example, employs a non-standard 6×16 filter format rather than the standard 8×12 filter format. If the user wants the benefit of reduced time for sample preparation and analysis, the user is locked into the filter medium produced by a particular manufacturer. The user cannot employ the filter of his or her choice. Moreover, since the crosstalk reducing pattern is built into the filter medium itself and the filter medium is discarded following use, the crosstalk reducing pattern and its manufacturing cost are consumed with the discarded filter medium. Yet another drawback of this technique is that the analyzed product, i.e., a bag containing a treated filter medium, is not in the microplate format. Thus, the filter medium in this technique cannot be used in any applications requiring the microplate format. A related drawback is that various types of ancillary equipment used in assays, including washing, dispensing, and stacking equipment, are adapted to operate with the microplate format. Since the filter medium in this technique is not included in a device having the microplate format, the filter medium cannot be used with such ancillary equipment.

Accordingly, there exists a need for a microplate assembly and method which overcomes the above-noted drawbacks associated with existing techniques.

SUMMARY OF THE INVENTION

A primary object of the present invention is to provide a microplate assembly and method which permits a filter medium chosen by a user to be placed in the microplate assembly.

Another object of the present invention is to provide a microplate assembly and method which permits a filter medium to be placed in the microplate assembly for sample preparation, analysis and counting. Since the microplate assembly is constructed in the microplate format, the filter medium may be used in any applications or ancillary equipment requiring the microplate format.

Yet another object of the present invention is to provide a microplate assembly and method which permits samples captured on a filter medium to be prepared, analyzed and counted in the microplate assembly with relatively high throughput.

Still another object of the present invention is to provide a microplate assembly and method which permits samples captured on a filter medium to be prepared, analyzed and counted accurately and inexpensively.

A further object of the present invention is to provide a microplate assembly and method which is cost-effective and easy to manufacture.

Other objects and advantages of the present invention will become apparent upon reading the following detailed description and upon reference to the accompanying drawings.

In accordance with the present invention, the foregoing objects are realized by providing a microplate assembly for use in analyzing samples captured on a filter medium having an upper and lower surface, comprising a holding tray having a bottom wall and side walls connected to the bottom wall, the holding tray receiving therein the filter medium with the lower surface adjacent to the bottom wall of the holding tray; and a collimator abutting the upper surface of the filter medium, the collimator being disposed substantially parallel to the bottom wall of the holding tray, the collimator having wells formed therein for surrounding the samples on the filter medium. Variably relatively positionable cooperating engagement structure is formed on the collimator and the holding tray for maintaining the collimator and the holding tray in an assembled condition in one of at least two relative positions, dependent upon the thickness of the filter medium, with the filter medium engaged between the wells of the collimator and the recessed surface of the holding tray, so as to accommodate filter mediums over a range of thicknesses.

The present invention further provides that in a microplate assembly using a holding tray and a collimator having sample wells formed therein, a method of preparing samples for analysis, the method comprising the steps of capturing the samples on a filter medium, placing the filter medium in the holding tray, adding scintillation cocktail or luminescent substrate to the filter medium, and placing the collimator over the holding tray with the filter medium positioned therebetween so that the samples are prepared for analysis.

DETAILED DESCRIPTION OF THE PREFERRED EMBODIMENT

Figure 1:
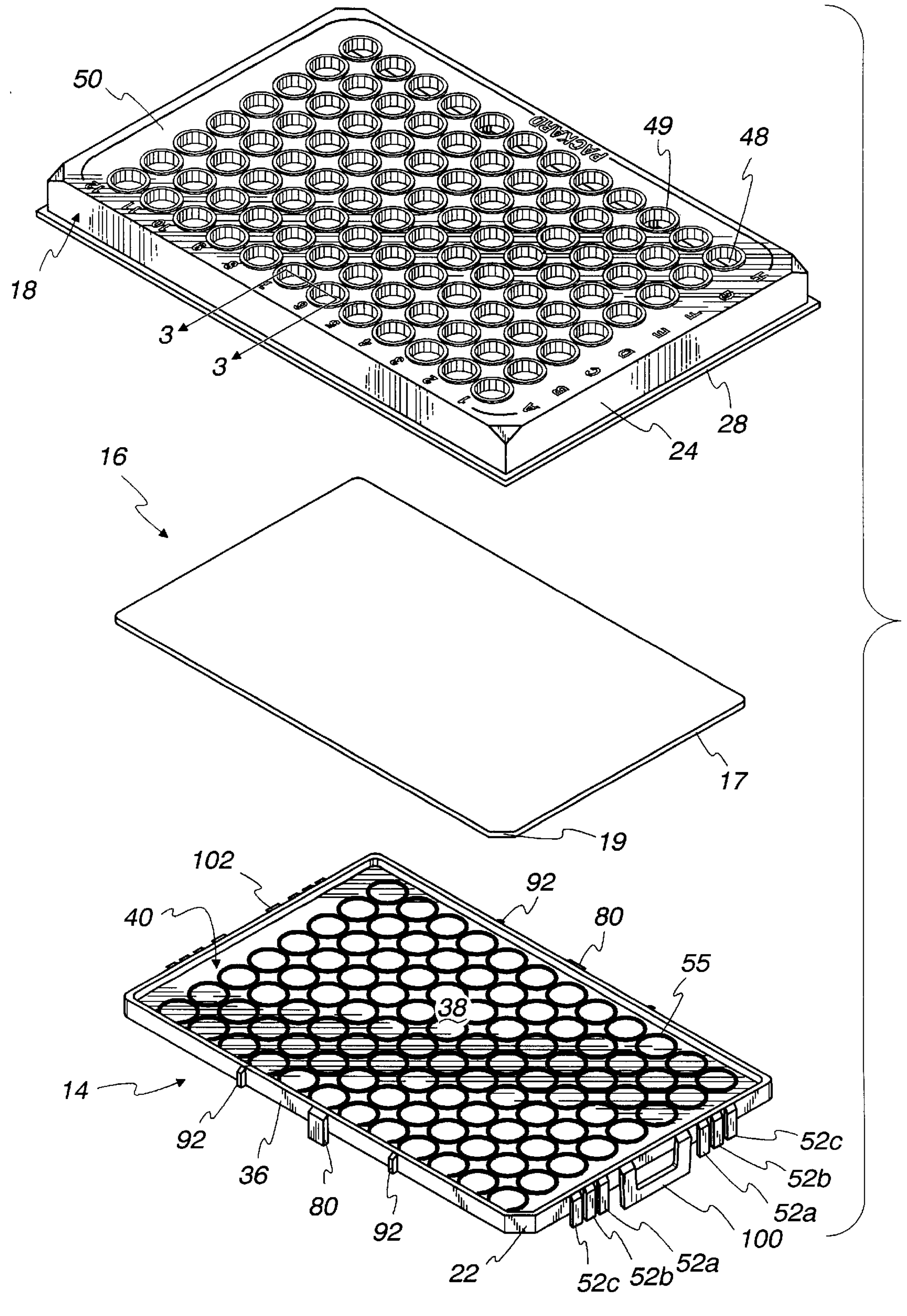
FIG. 1 is an exploded perspective view of a microplate assembly embodying the present invention.
Figure 2:
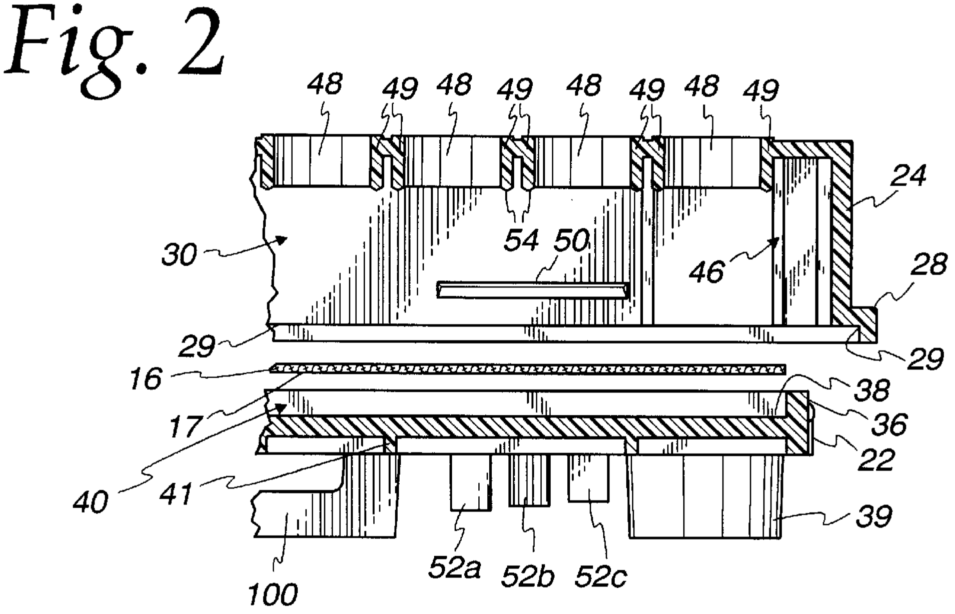
FIG. 2 is an enlarged exploded partial cross-section of the microplate assembly in FIG. 1.
Figure 3:
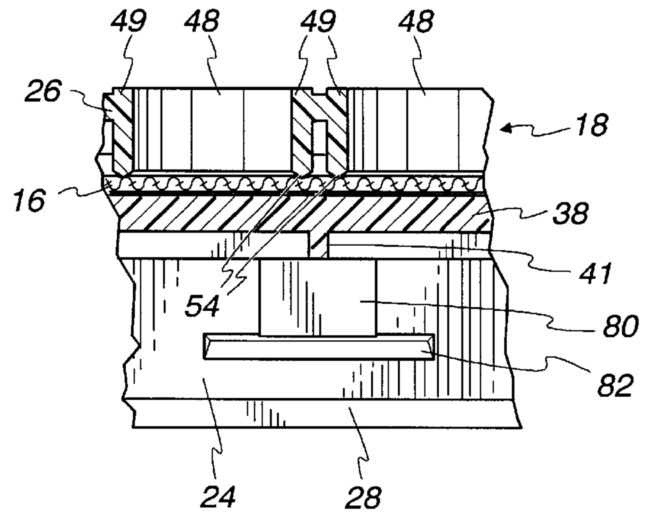
FIG. 3 is a partial sectional assembled view of the microplate assembly of FIG. 1.

Turning now to the drawings, FIGS. 1 through 3 illustrate a microplate assembly 10 including a holding tray 14, a filter medium 16, and a collimator 18. These elements are sized to stack on top of one another as indicated in FIG. 1. In particular, the medium 16 is positioned on the holding tray 14 beneath the collimator 18, and the collimator 18 is engaged over the holding tray 14.

The collimator 18 has a generally rectangular shape with an internal keyed corner in the form of an inwardly projecting rib 46. The filter medium 16 and the holding tray 14 have complimentary keyed corners 19, 22 permitting easy location and positive positioning of these elements during assembly of the microplate assembly 10. The collimator 18 includes a peripheral side wall 24 and a top surface 26 integrally connected to a central section of the side wall 24, and the side wall 24 includes a peripheral foot 28. The side wall 24 and its foot 28 extend around the periphery of the generally rectangular top surface 26, which permits another microplate assembly to be stacked beneath the assembly 10 with the upper surface of its collimator engaging a peripheral rim 29 formed in an undersurface of the foot 28. The top surface 26 and the side wall 24 form a rectangular compartment 30 for receiving the holding tray 14 therein.

The collimator and the holding tray 14 are preferably constructed of molded solvent-resistant plastic so that they may be reused.

The holding tray 14 and the collimator 18 are preferably constructed and arranged so that the microplate assembly 10 is in standard microplate format. For example, the dimension of the side wall 24 and the peripheral foot 28 are part of the standard microplate format. In particular, the outer dimensions of the foot are approximately 5.03 inches long and 3.37 inches wide. The side wall 24 and foot 28 together are approximately 0.55 inches in depth. Both the base 26 and the side wall 24 have a thickness of approximately 0.05 inches. With the foregoing construction, the collimator 18 acts as an adapter which conforms the microplate assembly 10 to standard microplate format.

Figure 4:
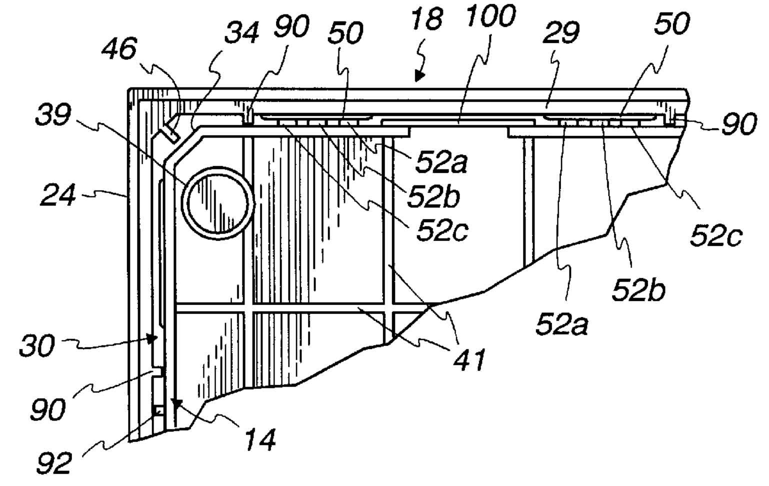
FIG. 4 is a partial bottom planned view showing further details of the assembly thereof.

The holding tray 14 has a generally rectangular shape sized to fit within the rectangular compartment 30 of the collimator 18. The holding tray 14 has a keyed corner 22 to facilitate placement of the holding tray 14 within the rectangular compartment 30. When the holding tray 14 is held within the rectangular compartment 30 of the collimator 18, the outside surface of the keyed corner 22 abuts the inside edge of the keyed corner or rib 46 of the collimator 18. The holding tray 14 has four side walls 36 and a recessed surface 38 integrally connected to the side walls 36. The side walls 36 and the recessed surface 38 form a generally rectangular compartment 40 for receiving the filter medium 16 therein. The underside of the holding tray 14 has four downwardly extending supporting feet 39 located adjacent its four corners, and may also be provided with a grid of support ribs 41 (see FIG. 4). Additional projecting support posts (not shown) of the same height as feet 39 are also provided midway between the feet 39 along the longer sides of the tray 14.

The outer length and width dimensions of the holding tray 14 are slightly smaller than the inner dimensions of the rectangular compartment 30 of the collimator 18 so that the holding tray 14 fits within the rectangular compartment 30. Since the holding tray 14 contacts liquids during assays, it is, as mentioned above, made of a solvent-resistant plastic to permit long-term reuse, thereby reducing assay costs.

The filter medium 16 is a filtration or hybridization media preferably with a thickness ranging from 0.005 inches to 0.020 inches. The microplate assembly 10 allows virtually any filter medium 16 chosen by a user to be analyzed, including glass fiber, nylon, nitrocellulose, phosphocellulose, or other suitable material. The filter medium 16 is cut to the size and geometry of the rectangular compartment 40 in the holding tray 14 either before or after collection or hybridization of the labeled samples. The filter medium 16 may be cut using a generally rectangular cutting template (not shown) so that the filter has a keyed corner 19 matching the inside surface (i.e. inner surface of wall 36) of the keyed corner 32 of the holding tray 14. In order for the filter medium to be cut to fit snugly within the rectangular compartment 40 in the holding tray 14, the template has length and width dimensions which are slightly smaller than the length and width dimensions of the rectangular compartment 40. After cutting the filter medium 16 and capturing the labeled samples, the filter medium 16 is placed into the rectangular compartment 40 of the holding tray 14 with a lower surface 17 of the filter medium 16 abutting the recessed surface 38 of the holding tray 14.

The collimator 18 is positioned over the filter medium 16 within the rectangular compartment 40 of the holding tray 14. To achieve a tight fit between the collimator 18 and the holding tray 14, while accomodating a filter medium 16 of any of a range of thickness dimensions, number of additional structural features of these two parts are provided, as will be more fully described below.

The collimator 18 is provided with through openings or wells 48 for preparation and analysis of the samples on the filter medium 16 beneath the collimator 18. In the preferred embodiment, the collimator 18 includes ninety-six wells arranged in an eight-by-twelve matrix. The centers of the wells 48 are spaced approximately 0.35 inches apart, and each of the wells 48 has a diameter of approximately 0.28 inches. To achieve proper alignment of the samples with the wells 48, the samples are prepared on the filter medium 16 in an eight-by-twelve matrix having substantially the same spatial dimensions as the wells 48. Thus, when the collimator 18 is placed over the filter medium 16 within the tray compartment 40, the ninety-six samples are aligned with the ninety-six wells. The top of each of the wells 48 includes an upper rim 49 to minimize crosstalk between the wells 48 at their tops, as described below.

When the samples in the microplate assembly 10 are counted in a scintillation counter, the wells 48 act to channel or collimate or reflect signals produced by the interaction of the samples and scintillation fluid or luminescent substrate within the filter medium 16 into photodetectors contained in the scintillation counter. During counting, these photodetectors of the scintillation counter are positioned above the individual wells and may be interlocked with the upper rims 49 of the wells 48 to minimize crosstalk between the wells 48 at their tops while counting with the scintillation counter. More specifically, the interlocking relationship between the photodetectors and the upper rims 49 prevents signals from one well intended for the photodetector interlocked with that well from escaping that well and being detected by a photodetector associated with another well. Also, the interlocking relationship prevents a photodetector interlocked with one well from detecting signals other than those associated with that well.

The wells 48 are further provided with respective lower rims 54 extending from the respective lower circular peripheries of the wells 48. The lower rims 54 drive or "dig" into the filter medium 16 beneath the collimator 18. Once the wells 48 are aligned with the samples on the filter medium 16, the lower rims 54 fix the horizontal position of the filter medium 16 relative to the collimator 18. The lower rims 54 prevent shifting of the filter medium 16 relative to the collimator 18, which might misalign the wells 48 relative to the samples. In addition, the lower rims 54 minimize crosstalk between the samples through the filter medium 16 by pressing into the filter medium 16 between the samples.

To optimize performance of the microplate assembly 10, the holding tray 14 and the collimator 18 are preferably optically opaque so as to maximize counting efficiency and reduce optical crosstalk for both low and high energy radionuclides as well as luminescent labels. For assays and labels requiring maximum light collection efficiency, the surface 38 of the holding tray 14 is provided with a highly reflective white surface to maximize signal. The surface 38 may be provided with antireflective elements, for example by being inscribed with ninety-six black circles 55 placed so they correspond directly to the ninety-six sample positions on the filter medium 16 and the ninety-six wells on the collimator 18, to reduce crosstalk. In the embodiment shown, the pattern of circles 55 for the holding tray 14 is printed, painted, or hot stamped directly onto the recessed upper surface 38 of the holding tray 14.

The reusability of the holding tray 14 and the collimator 18 significantly reduces the cost of many types of assays. To begin with, the crosstalk reducing elements, including the lower rims 54, the upper rims 49, and the pattern of circles 55, are built into the holding tray 14 and the collimator 18. Since the holding tray 14 and the collimator 18 are reusable, the expense of manufacturing these crosstalk reducing elements is not wasted or consumed following use of the filter medium 16. Furthermore, the samples on the filter medium 16 are analyzed while in the microplate assembly 10. No scintillation vials or associated volumes of scintillation fluid are consumed during the analysis. Except for the filter medium 16, the elements of the microplate assembly 10 are reusable and, therefore, their costs are not consumed following analysis of the filter medium 16.

Figure 5:
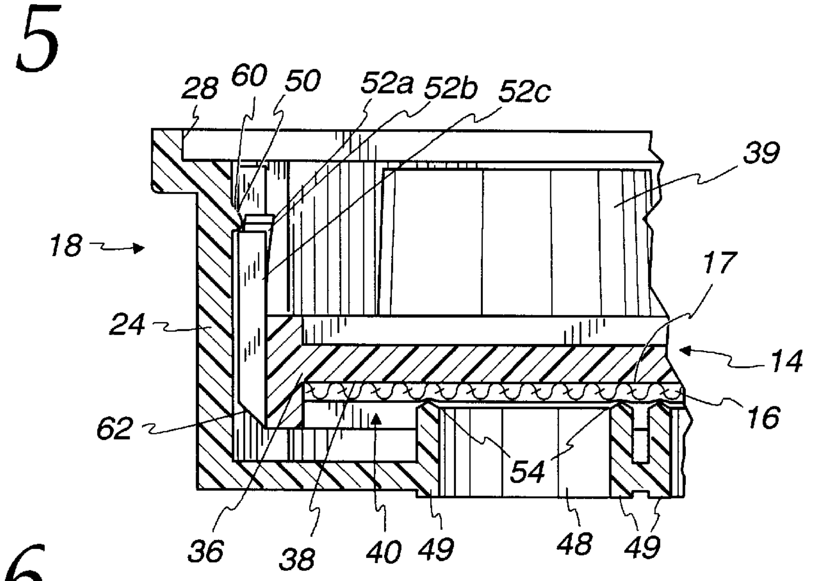
FIG. 5 is a partial sectional view showing a further detail of the assembly thereof.
Figure 6:
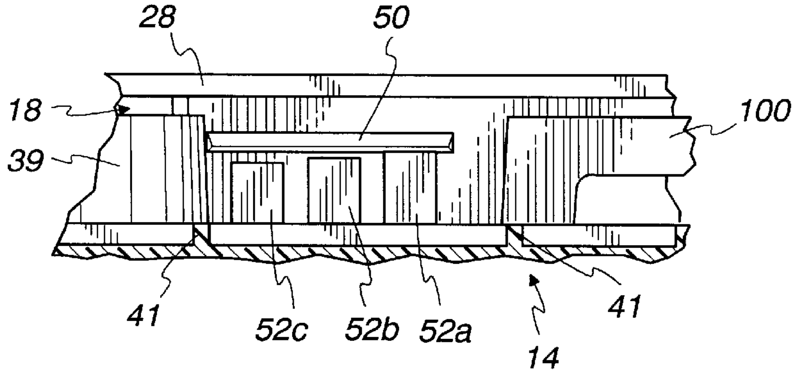
FIGS. 6–8 are partial sectional elevations showing further details of the assembly of a holding tray and collimator of the microplate assembly of the invention.
Figure 7:
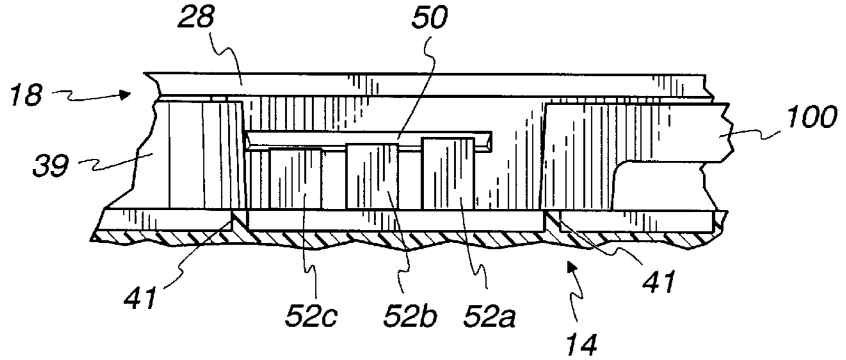

Referring now also to FIGS. 4 through 8, further details of the structure of the collimator 18 and the holding tray 14 are illustrated. The structural elements shown in FIGS. 4 through 7 define multiple relative assembled positions of the collimator and the holding tray for accommodating filter mediums of different thicknesses. FIGS. 5 through 7 are rotated 180° relative to FIGS. 1 through 3 and 8. In the embodiment shown herein, the collimator and the holding tray have a number of sets of complementary facing projecting surfaces on their respective side walls 24 and 36 which define multiple relative positions for engagement with each other, for accommodating different thicknesses of filter medium 16 therebetween.

More specifically, the inner surface of the side wall 24 of the collimator 18 includes at least two sets of inwardly projecting ridges 50 which are preferably formed on opposed ones of the side walls 24, and preferably the longitudinally opposed ones of the side walls 24. Cooperatively, the holding tray 14 has a like number of sets of outwardly projecting fingers 52*a,* 52*b,* 52*c* which are likewise formed on opposite side walls 36, and preferably on the longitudinally opposite side walls 36 of the holding tray 14. In the preferred embodiment illustrated, two such sets of cooperating projecting ribs 50 and fingers 52*a,* 52*b,* 52*c* are formed in each of the two longitudinally opposite side walls of the collimator 18 and the holding tray 14, respectively.

As best seen in FIGS. 6 and 7, each of the sets of projecting fingers 52*a,* 52*b,* 52*c* is preferably three in number, with each finger projecting beyond a peripheral edge part of the side wall 36 by a different amount. This projection permits the fingers 52*a,* 52*b,* 52*c* to resiliently deflect to allow passage of the ridge 50 past one or more thereof during assembly of the holding tray with the collimator. Thus, each of the three fingers 52*a,* 52*b,* 52*c* is of a different length from the other two in each set, however, with the three fingers of each of the four sets in the preferred embodiment being of the same three respective lengths.

Preferably, each of the fingers 52*a,* 52*b,* 52*c* has a ramped lead-in surface 62 and cooperatively, the ridges 50 have ramped lead-in surfaces 60 for facilitating initial movement of the fingers past the ridges 50 during assembly. Thus, for example, FIG. 6 indicates assembly of the holding tray 14 with the collimator 18 with the longest one 52*a* of the three fingers being engaged with the undersurface of the rib 50. However, FIG. 7 illustrates assembly with the shortest one of 52*c* of the fingers being engaged with an undersurface of the rib 50. Thus, FIGS. 6 and 7 between them illustrate the range of relative depths of assembly of the holding plate 14 relative to the collimator 18 for accommodating a corresponding range of thicknesses of filter medium 16 therebetween.

Figure 8:
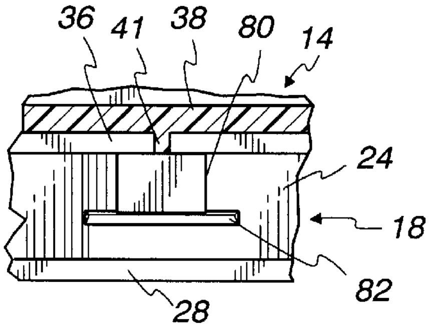

Referring also to FIG. 8, an additional set of projecting elements including a single finger 80 and a complementary raised rib or ridge 82 are preferably formed approximately at a midpoint at the two laterally opposed side walls 24 of the collimator 18 and 36 of the holding tray 14, respectively. These elements may snappingly ride over each other and inter-engage, and be provided with similar cooperatively ramped lead-in surfaces to those described for respective ribs 50 and fingers 52*a,* 52*b,* 52*c*. However, only a single length of such finger 80 is provided in the respective lateral side walls, and is of generally the same effective length as the shortest one 52*c* of the fingers 52*a,* 52*b,* 52*c*. The purpose of these additional elements 80 and 82 is to snappingly override each other so as to oppose disassembly of the holding plate relative to the collimator once the two are assembled with the filter medium 16 positioned therebetween as described above.

A number of outwardly projecting ribs 90, 92 are formed respectively at spaced locations about the inner side wall surface 24 of the collimator and outer side wall surface 36 of the holding tray 14, respectively to further properly center and position the two relative to each other upon assembly. These additional raised elements also accommodate the extra thickness of the respective fingers 52*a*, 52*b*, 52*c* and 80 and provide sufficient relief space for the action of the respective fingers 52*a*, 52*b*, 52*c* and 80 of the holding tray 14 as described above.

As mentioned above, the holding tray may further be provided with a number of downwardly projecting feet 39 for providing a stable support for the holding tray on a flat surface (not shown) during application of the filter medium to the recessed surface 40 thereof prior to assembly of the holding tray 14 with the collimator 18.

Preferably, a pair of additional generally U-shaped gripping members 100, 102 are provided at longitudinally opposite sides of the holding tray 14, and preferably centered between the respective sets of fingers 52*a*, 52*b*, 52*c* at each of these longitudinally opposite sides. These gripping means facilitate engagement of the holding tray for disassembly thereof from the collimator following conclusion of a test procedure, so that the spent filter medium 16 may be removed and the collimator and filter tray prepared as necessary before receipt of a new filter medium 16 for subsequent testing.

A general protocol is followed for preparing and analyzing samples in the microplate assembly 10. The filter medium 16 is processed using conventional protocols and cutting template is aligned over the filter medium 16. Using a sharp knife or blade around the periphery of the template 17, the filter medium 16 is cut to size.

The filter medium 16 is placed in the holding tray 14 with the complementary keyed corners properly oriented relative to one another. Scintillation cocktail or luminescent substrate may be added to the entire tray at this time or later on. While the amount of cocktail or substrate added depends upon the filter medium 16 being used, one to three milliliters of cocktail or substrate is preferred. Thicker filter media require greater volumes of cocktail or substrate, but the holding tray 14 should not be overfilled. It is only necessary to fully wet the entire filter medium 16.

Next, the collimator 18 is placed in the holding tray 14 over the filter medium 16. During this placement, the user should ensure that the keyed corners 22 and 46 are aligned and that the samples are centered within the appropriate wells. If the cocktail or substrate was not added previously, the cocktail or substrate is added to each of the wells 48 at this time using a multichannel pipet to conserve reagents. Ten to thirty-five microliters per well is preferred, again depending on the filter medium 16 being used. The foregoing general protocol for preparing samples for analysis takes relatively little time compared to the technique of cutting individual samples from filter media and placing the samples in individual scintillation vials, or the technique of exposing filter media to X-ray filtm for a period ranging from hours to days.

Samples contained in the microplate assembly 10 are analyzed and counted using a scintillation counter designed to count samples in the microplate format, i.e., in the microplate assembly 10. An example of such a scintillation counter is the TopCount® Microplate Scintillation and Luminescence Counter, commercially available from Packard Instrument Company. Counting samples while they are still in the microplate assembly 10 results in dramatically improved throughput because it avoids the need to cut individual samples from the filter medium 16 for counting the individual scintillation vials using a liquid scintillation counter (LSC). Not only does counting the samples while they are in the microplate assembly 10 result in improved throughput, but it also results in an accurate count, as demonstrated by the conducted experiment described below.

The basic performance of the microplate assembly 10 is measured by evaluating its counting efficiency and its ability to prevent crosstalk between sample wells. The counting efficiency is determined by counting the samples while they are in the assembly 10 using the TopCount® counter and by comparing the resulting count to a count obtained using a conventional LSC. Counting efficiency is calculated by dividing the CPM (counts per minute) of the TopCount® counter by the DPM (disintegrations per minute) of the LSC. Crosstalk is determined by dividing the average CPM of the eight wells surrounding an active well by the CPM of the active well, where crosstalk includes both optical and radiation components.

The microplate assembly 10, in conjunction with a scintillation counter such as the TopCount® counter designed to count the samples while they are still in the assembly, provides excellent absolute counting efficiencies for samples immobilized on filter media. Thus, the microplate assembly 10 permits samples captured on filter media to be analyzed and counted accurately, in addition to quickly and inexpensively. Accurate quantitation can be achieved over a wide dynamic range. Furthermore, the design of the microplate assembly 10 virtually eliminates crosstalk caused by photon transmission.

The microplate assembly 10 permits the analysis of many assays in which the radio or luminescent label is immobilized on a variety of filter media. The microplate assembly 10 allows a user to choose the filter medium most appropriate for the application. Since the microplate assembly 10 is constructed in the microplate format, the filter medium 16 may be used in a variety of applications and ancillary equipment requiring the microplate format. The user is not limited to choosing a particular filter medium which may only be used in limited equipment.

While the invention may be susceptible to various modifications and alternative forms, specific embodiments have been shown and described herein above by way of example. It should be understood, however, that it is not intended to limit the invention to the particular forms disclosed. On the contrary, the intention is to cover all modifications, equivalents and alternatives falling within the spirit and scope of the invention as defined by the dependent claims.

What is claimed is:

1. A microplate assembly for use in analyzing samples captured on a filter medium having an upper and lower surface, comprising:

a holding tray having a recessed surface and side walls connected to said recessed surface, said holding tray receiving therein the filter medium with the lower surface adjacent to said recessed surface of said holding tray;

a collimator abutting the upper surface of the filter medium, said collimator being disposed substantially parallel to said recessed surface of said holding tray, said collimator having wells formed therein for surrounding the samples on the filter medium; and variably relatively positionable cooperating engagement means formed on said collimator and said holding tray for maintaining said collimator and said holding tray in an assembled condition in one of at least two relative positions, dependent upon the thickness of said filter medium, with said filter medium engaged between the wells of said collimator and the recessed surface of said holding tray, so as to accommodate filter mediums over a range of thicknesses.

2. The microplate assembly of claim 1, wherein said collimator has side walls dimensioned for surrounding said holding tray side walls and wherein said cooperating engagement means comprises a plurality of sets of complementary facing projecting surfaces on said collimator side walls and said holding tray side walls respectively, the projecting surfaces on said collimator side wall and said holding tray side walls defining multiple relative positions for engagement with each other.

3. The microplate assembly of claim 2 wherein said projecting surfaces comprise at least two sets of inwardly projecting ridges formed on opposite ones of the side walls of said collimator and, at least two sets of outwardly projecting fingers, each comprising at least two fingers of different length, formed on opposite ones of the side walls of said holding tray and positioned for alignment with said ridges.

4. The microplate assembly of claim 3 wherein said fingers project beyond peripheral edge parts of said side walls of said holding tray so as to resiliently deflect to allow passage of said ridges and thereafter, at least one of said fingers resiliently returning to engage a trailing surface of said ridge.

5. The microplate assembly of claim 3 wherein said fingers have ramped lead-in surfaces for facilitating initial movement thereof past said ridges.

6. The microplate assembly of claim 3 wherein said ridges have ramped lead-in surfaces for facilitating initial movement of the fingers thereby.

7. The microplate assembly according to claim 3 wherein each of said sets of fingers is three in number, each of said three fingers being of a different length from the other two fingers of the same set and of like length to one of the fingers in each of the other sets.

8. The microplate assembly of claim 3 wherein said sets of projecting ridges and fingers are located respectively at longitudinally opposite ones of said side walls of the collimator and holding tray.

9. The microplate assembly of claim 8 and further including at least one additional raised ridge and complementary finger on each of the remaining laterally opposed side walls of said collimator and said holding tray.

10. The microplate assembly of claim 1 and further including projecting gripping means on said holding tray for facilitating engagement thereof for disassembly from said collimator.

11. The microplate assembly of claim 1, wherein said holding tray and said collimator include complementary keyed corners for aligning said holding tray and said collimator relative to one another.

12. The microplate assembly of claim 1, wherein said side walls and said recessed surface of said holding tray form a generally rectangular compartment for receiving the filter medium therein.

13. The microplate assembly of claim 1, wherein said wells of said collimator are arranged in a matrix corresponding to the arrangement of the samples on the filter medium so that each of said wells surrounds a separate sample.

14. The microplate assembly of claim 1, wherein said wells of said collimator include respective lower rims protruding from the respective lower peripheries of said wells into the filter medium to minimize crosstalk through the filter medium.

15. The microplate assembly of claim 1, wherein each of said wells of said collimator includes an upper rim formed around the upper periphery thereof to minimize crosstalk between said wells.

16. The microplate assembly of claim 1, wherein said holding tray and said collimator are reusable.

17. The microplate assembly of claim 1, wherein the filter medium is cut to the size and shape of the recessed surface of said holding tray so that the filter medium fits snugly within the recessed surface of said holding tray.

18. The microplate assembly of claim 1, wherein said recessed surface of said holding tray is provided with anti-reflective elements to reduce crosstalk between said samples.

19. The microplate assembly of claim 18, wherein said anti-reflective elements comprise a plurality of dark circles inscribed on said recessed surface of said holding tray alignable with the wells of said collimator.

20. The microplate assembly of claim 1 wherein said recessed surface of said holding tray is reflective.

21. The microplate assembly of claim 20, wherein said recessed surface of said holding tray is provided with anti-reflective elements to reduce crosstalk between said samples.

22. The microplate assembly of claim 21, wherein said anti-reflective elements comprise a plurality of dark circles inscribed on said recessed surface of said holding tray alignable with the wells of said collimator.

* * * * *